United States Patent
Keaty, Jr. et al.

(10) Patent No.: US 7,717,889 B2
(45) Date of Patent: May 18, 2010

(54) DISINFECTANT DELIVERY SYSTEM AND METHOD OF PROVIDING ALCOHOL FREE DISINFECTION

(75) Inventors: Thomas Keaty, Jr., Crystal Lake, IL (US); Barbara T. Skiba, Chicago, IL (US); Paul H. Hanifi, Barrington Hills, IL (US)

(73) Assignee: Sage Products, Inc., Cary, IL (US)

( * ) Notice: Subject to any disclaimer, the term of this patent is extended or adjusted under 35 U.S.C. 154(b) by 657 days.

(21) Appl. No.: 11/426,611

(22) Filed: Jun. 27, 2006

(65) Prior Publication Data

US 2006/0233868 A1 Oct. 19, 2006

Related U.S. Application Data

(63) Continuation of application No. 10/435,902, filed on May 12, 2003, now Pat. No. 7,066,916.

(51) Int. Cl.
*A61M 35/00* (2006.01)
*A61F 13/00* (2006.01)
*A61K 9/70* (2006.01)

(52) U.S. Cl. ............... 604/290; 604/289; 424/443

(58) Field of Classification Search ........... 604/289, 604/290; 424/443, 445, 447, 449

See application file for complete search history.

(56) References Cited

U.S. PATENT DOCUMENTS 5,690,958 A * 11/1997 McGrath ............ 424/451
6,029,809 A *  2/2000 Skiba et al. .......... 206/210

\* cited by examiner

*Primary Examiner*—Melanie J Hand
(74) *Attorney, Agent, or Firm*—Barnes & Thornburg LLP

(57) ABSTRACT

A disinfectant delivery system and method of providing alcohol-free disinfection to a body to be disinfected, as well as a method of infection reduction by preparation of a patient before an invasive procedure. A blended cloth comprising first fibers and second fibers is provided with the first fibers generally being greater in quantity by weight than the second fibers. A disinfectant solution impregnates the blended cloth, with the disinfectant solution having chlorhexidine gluconate as an active ingredient and having no alcohol. In the method according to the invention, at least one impregnated blended cloth is used to disinfect at least a portion of a body. A plurality of blended cloths can be provided for disinfecting discrete portions of the body. When an invasive procedure is to be performed on a patient, a further method according to the invention of infection reduction comprises using a CHG-impregnated cloth to disinfect at least a portion of the patient at least one day prior to the invasive procedure proximate the location of the invasive procedure.

10 Claims, 2 Drawing Sheets

FIG. 1
FIG. 2
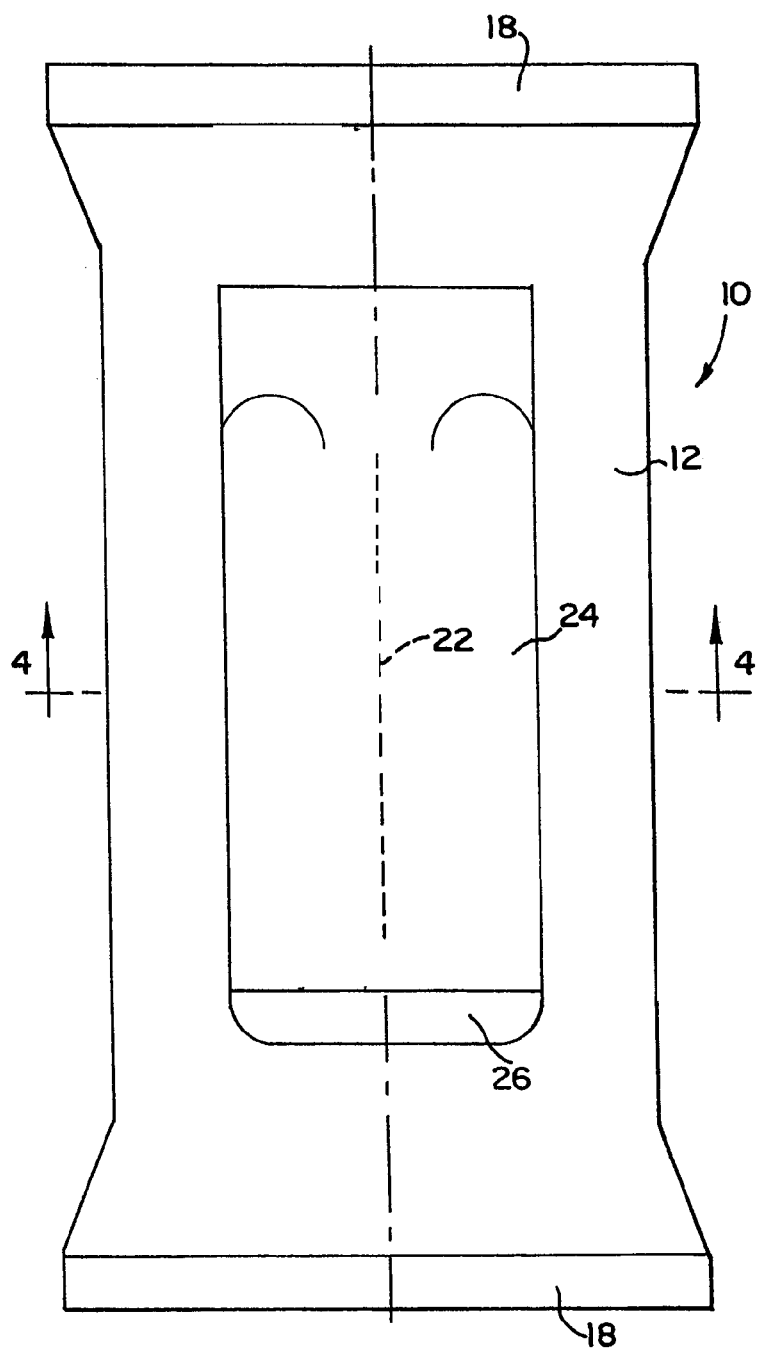
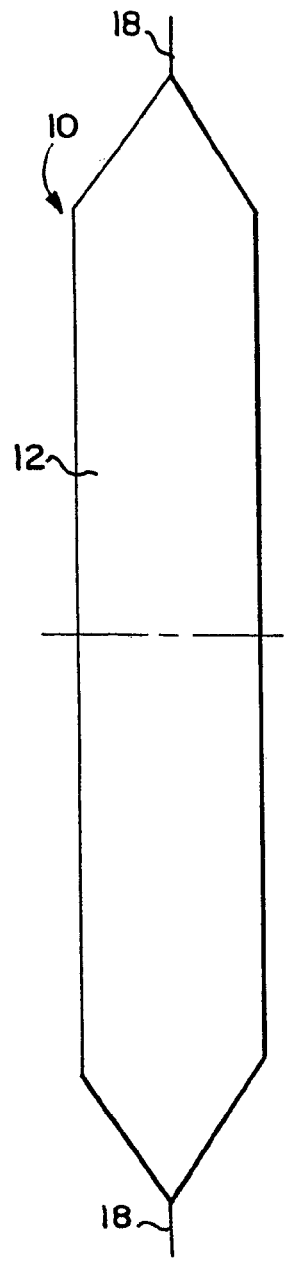

DISINFECTANT DELIVERY SYSTEM AND METHOD OF PROVIDING ALCOHOL FREE DISINFECTION

RELATED APPLICATION

This application is a continuation of U.S. patent application Ser. No. 10/435,902, filed May 12, 2003, now U.S. Pat. No. 7,066,916.

BACKGROUND OF THE INVENTION

This invention relates to disinfection and in particular to a disinfectant delivery system and a method of providing alcohol-free disinfection to a body to be disinfected. The invention also relates to a method of infection reduction by preparation of a patient before an invasive procedure.

Resistant organisms, such as MRSA and VRE, are an increasing problem in modern health care facilities. Once a patient becomes colonized and acquires an infection from a resistant organism, it is difficult and costly to treat the infection. The result has been a significant increase in morbidity and mortality for health care facilities.

Previously, it has been known to provide a patient bathing system having washcloths for body cleansing. U.S. Pat. Nos. D 394,605; 5,725,311; 5,906,278; 5,956,794 and 6,029,809, all assigned to the assignee of the present application, are directed to such a system. A resealable package is provided having a plurality of washcloths contained therewithin. The package has an opening through which washcloths can be individually withdrawn for body cleansing. The package can be heated, such as in a microwave or other heating facility, so that withdrawn washcloths are comfortable to the patient when used.

Such a system and washcloths are convenient and effective for body cleansing. However, until the present invention, microbial disinfection has not been possible with such a system.

Chlorhexidine gluconate (CHG) is a highly effective broad-spectrum topical antiseptic. It is effective against both gram-positive and gram-negative bacteria. In addition, CHG exhibits the property of persistence in that it continues its anti-microbial activity beyond immediate bacteria elimination, providing protection several hours beyond an initial application. Moreover, CHG exhibits a cumulative property that improves efficacy after multiple applications. Finally, CHG is well-tolerated on human skin. It is currently considered to be the premiere topical antiseptic ingredient by the health care community.

Pre-surgical or skin puncture preparation requires delivery of an antiseptic to the body area being prepared for an invasive procedure. CHG has been used in the past in pre-surgical preparations, although each such preparation employs alcohol as an active ingredient. Never has CHG been used alone as the active ingredient of a pre-surgical preparation, nor has CHG of any nature ever been delivered via a pre-impregnated disposable washcloth.

When skin bacteria is to be reduced, a pre-surgical preparation is applied to the patient's skin immediately before the surgical procedure. One method also attempted in the past, but not in widespread use, is to apply topical antiseptics to the entire body several days prior to the surgical procedure, which, in theory, reduces skin bacteria levels even before a pre-surgical preparation is applied. The combination seems to further reduce post-surgical infection.

SUMMARY OF THE INVENTION

In one form, the invention is directed to a disinfectant delivery system, which comprises a blended cloth comprising first fibers and second fibers. The quantity by weight of the first fibers is generally greater than the quantity by weight of the second fibers, and the absorbency by weight is greater than weight of the blended cloth. A disinfectant solution impregnates the blended cloth with the disinfectant solution having chlorhexidine gluconate as an active ingredient and having no alcohol.

In accordance with the preferred form of the invention, the fibers are blended by entanglement, and comprise polyester. Preferably, the first fibers have one thickness and the second fibers have a thickness that is different than the one thickness. In the disclosed embodiment of the invention, the first thickness is about 1.2 to 1.5 denier. The second thickness is about 4.75 denier. In all forms of the invention, the fibers have a length of from about 1.5 to 3 inches.

The CHG is present in about 1.80 to 2.20 percent by weight of the disinfecting solution. Preferably the CHG is 2 percent by weight, but it has been found effective in the range just explained.

In the method according to the invention, the blended cloth is provided, as well as a disinfecting solution having chlorhexidine gluconate as an active ingredient with no alcohol. The cloth is impregnated with the disinfecting solution, and the impregnated cloth is then used to disinfect at least a portion of a body.

In another preferred form of the invention, a plurality of the blended cloths are provided, all of which are impregnated by the disinfecting solution. Then, when used, each of the impregnated cloths is used to disinfect a discrete portion of the body. The cloths can be provided packaged in a resealable package before use, or can be impregnated immediately prior to use.

In yet another form of the invention, infection reduction is accomplished by preparation of a patient before an invasive procedure. A blended cloth is provided, comprising a fibrous mat which is impregnated with the disinfecting solution having chlorhexidine gluconate as an active ingredient and having no alcohol. The impregnated cloth is then used to disinfect at least a portion of the patient at least one day prior to the invasive procedure proximate the location of the invasive procedure.

Preferably, the blended cloth according to the invention is used as the fibrous mat, and a plurality of cloths are provided in a package, so that each cloth can be used to disinfect a discrete portion of the patient at least one day prior to the invasive procedure.

BRIEF DESCRIPTION OF THE DRAWINGS

The invention is described in greater detail in the following description of examples embodying the best mode of the invention, taken in conjunction with the drawing figures, in which:

FIG. 1 is a top plan view of one form of a disinfectant delivery system according to the invention;

FIG. 2 is a side elevational view thereof,

DESCRIPTION OF EXAMPLES EMBODYING THE BEST MODE OF THE INVENTION

Figure 3:
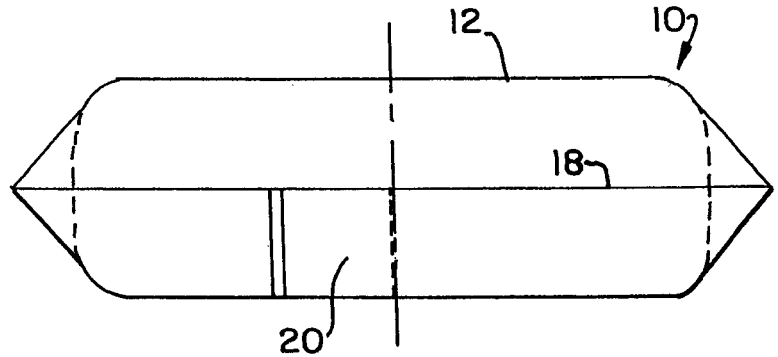
FIG. 3 is an end elevational view thereof.

A disinfectant delivery system having blended cloths according to the invention is shown generally at 10 in the drawing figures. The system 10 includes three components, a sealed, hollow, flexible outer package 12, an insulating and supporting layer 14, and a plurality of blended cloths 16.

Figure 4:
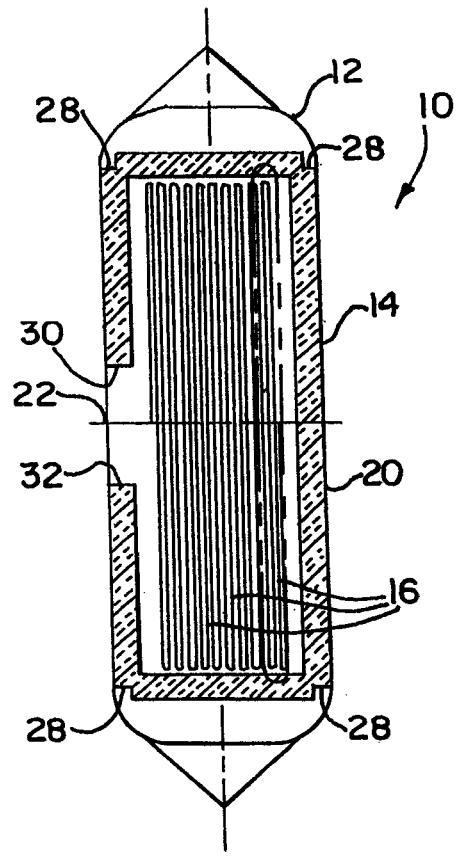
FIG. 4 is a cross-sectional view thereof, taken along lines 4-4 of FIG. 1.
Figure 5:
FIG. 5 is an elevational view of one of the blended cloths according to the invention, shown surrounded by phantom lines in FIG. 4.

U.S. Pat. Nos. 5,275,311; 5,906,278; 5,956,794 and 6,029,809, the disclosures of which are incorporated herein by reference, illustrate earlier forms of structures similar to those of the present application, when used in connection with a patient bathing system. As explained in the incorporated patents, the outer package 12 is preferably formed from thin, plastic film in an elongated fashion having a generally rectangular cross section as shown in FIG. 4. A package has end heat seals 18 and a longitudinal heat seal 20. The package 12 may be conventional.

The outer package 12 also includes an elongated dispensing slit 22. It may be sealed in many conventional fashions, and in one form, a seal in the form of a label 24 is applied to the outer package over the slit 22. The label 24 can be conventional or as described in incorporated U.S. Pat. No. 5,725,311. The label 24 also includes a free end 26 which is free to be grasped by a user for peeling the label 24 to expose the slit 22.

The insulating and supporting layer 14 is depicted in FIG. 4. It preferably comprises a foam sheet which has been shaped to conform to the interior of the outer package 12. For shaping purposes, a series of lateral slits 28 are formed in the foam sheet in general registration with the corners of the outer package 12, as explained in incorporated U.S. Pat. No. 5,906,278.

The insulating layer 14 terminates at opposite ends 30 and 32. The end edges 30 and 32 are disposed on opposite sides of the elongated dispensing slit 22 to permit access to the interior of the package 12, if the insulated layer 14 is utilized. In instances where heating of the interior of the outer package 12 is unnecessary, or where maintenance of temperature after heating is not needed, the insulating layer 14 may be eliminated.

The blended cloths 16 are individual, folded structures which are stacked one atop the other for individual dispensing through the dispensing slit 22. The cloths 16 are absorbent and are impregnated with a disinfectant solution. The cloths 16 have a sufficient porosity to hold a desired amount of the disinfectant solution, which is uniformly dispersed as explained below.

Each of the cloths 16 comprises a blended cloth comprising first fibers and second fibers, with the quantity by weight of the first fibers being generally greater than the quantity by weight of the second fibers. The blended cloth 16 has an absorbency by weight much greater than the weight of the blended cloth. Preferably, the fibers of the blended cloth 16 are polyester. The first fibers have one thickness and the second fibers have a second thickness that is different from that of the first fibers. In accordance with the preferred form of the invention, the thickness of the first fibers is about 1.2 to 1.5 denier. The thickness of the second fibers is greater, at about 4.75 denier. All of the fibers have a length from about 1.5 to 3 inches. In a particularly preferred form of the invention, the first fibers constitute 70 percent of the blend by weight, while the second fibers constitute 30 percent of the blend by weight. The cloth 16 is densely blended and has an absorbency of water much greater by weight than the weight of the blended cloth, with the absorbency being at least eight times by weight, and preferably over ten times by weight.

The fibers are generally round in cross-section, and when mechanically entangled together have a tensile strength of 20 pounds per inch, or greater. The fibers, when concentrated by mechanical entanglement, have a density of about 4.3 ounces per square yard to about 5.3 ounces per square yard for a cloth having an average thickness of 0.090 inches. The preferred concentration for an optimal cloth of this thickness is about 4.8 ounces per square yard.

The blended cloths 16 can have a thickness from about 0.055 inches to 0.125 inches, with the preferred thickness being about 0.090 inches. Other thicknesses can be employed so long as the absorbency and concentration of the fibers are within the parameters set forth herein.

The disinfectant solution utilizes chlorhexidine gluconate (CHG) as the active ingredient. CHG has been employed for several reasons. First, CHG is a highly effective broad-spectrum topical antiseptic that has been shown to be effective against both gram-positive and gram-negative bacteria. Second, CHG exhibits the property of persistence. It continues its anti-microbial activity beyond the immediate purge of the treated area, providing protection for hours beyond initial application. Third, CHG exhibits a cumulative property that improves efficacy after multiple applications. Fourth, CHG is well-tolerated on human skin. Other equivalent disinfectant solutions can be employed, but such solutions must exhibit the four qualities just mentioned.

In addition, CHG has an affinity for certain types of fibers, and the polyester structure of the blended cloth 16 has been tested to release all of the CHG when used. The CHG solution is alcohol-free, in that no alcohol of any nature is employed, unlike all previous solutions using CHG, which have always had alcohol as an active and major ingredient. It is thought that the combination of the unique blend of fibers and CHG leads to the superior combination according to the invention.

One disinfectant solution according to the invention comprises 2 percent CHG with a water base. In percent by weight, in such an example, water constitutes 73.25 percent, and a 20 percent CHG solution comprises 10.90 percent. Two other ingredients are available in significant percents, propylene glycol at 3.10 percent and glycerin at 2.50 percent. Other minor ingredients, including aloe vera, dimethicon 350 cst, igepal CO 630, polysorbate 20, shaw mudge fragrance and glucono delta lactone constitute, in the aggregate, less than 1 percent. In preparing the solution, 13.25 percent water by weight is retained, and all remaining ingredients except for the 20 percent CHG are mixed. Then, the 20 percent solution of CHG and the final 13.25 percent water are added, and the entire solution is mixed to form the disinfectant solution according to the invention. Finally, the disinfectant solution is used to impregnate the blended cloths 16. The disinfectant solution is evenly dispersed throughout each of the blended cloths 16 in either packaged form, as shown in the drawing figures, or the disinfectant solution can be added to dry cloths 16 at a later time. The preferred delivery system is a package as shown in the drawing figures containing at least one of the blended cloths 16.

The invention can uniquely be used to provide infection reduction by preparation of a patient before an invasive procedure, such as surgery, introduction of a catheter, or any procedure that is intended to pierce the skin in any manner. Any such procedure will be termed herein as surgical site preparation, and it has been found that surgical site infections can be greatly reduced by utilizing the invention at least one day prior to the invasive procedure. The standard method of reducing skin bacteria is to use a pre-surgical preparation on patient's skin immediately before the surgical procedure. The invention of the present application can be used at least one day, and even more, before the surgical procedure, which cumulatively reduces skin bacteria levels even before pre-surgical preparation occurs immediately prior to surgery or a similar invasive procedure. This combination further reduces the post-surgical infection rate beyond a simple standard pre-surgical preparation.

The method according to the invention is unique in that the disinfecting solution having CHG is applied as a "no-rinse" solution without a shower or bath to dilute the ingredients, and it can be applied in the vicinity of the future invasive procedure, or over the entire body. Preferably, the blended cloths having the CHG disinfecting solution are applied sequentially to all body parts to lower the total skin bacteria count on the body about a day or more in advance of the invasive procedure. Then, at the time of the invasive procedure, standard preparation of the patient's skin is performed in the normal manner.

ACHIEVEMENTS

The invention provides a unique, no-rinse disinfectant delivery system comprising blended cloths 16 impregnated with a disinfectant solution having only CHG as the active ingredient, without alcohol. In the past, CHG has been used as a topical disinfectant, but always with alcohol, and never in a combination comprising a pre-impregnated disposable washcloth.

By using the system according to the invention for full-body disinfection (such as with one cloth for each of the arms, one cloth for each of the legs, a cloth for the trunk, and a cloth for the perineum and buttocks), the cycle of skin colonization with resistant organisms is broken, reducing the spread of organisms to the environment and to the health care workers. This greatly reduces the risk of spreading resistant organisms throughout a health care facility.

The risk of infection is reduced by the invention when a patient is prepared a day, and sometimes days, in advance of an invasive procedure. With the CHG-containing disinfectant solution applied sequentially to all body parts, the total skin bacteria count is reduced, and with normal preparation before an invasive procedure, the post-surgical infection rate experienced by patients is reduced beyond that of standard preparation of a patient immediately prior to an invasive procedure.

The blended cloth 16, comprising a unique blend of all polyester fibers, permits delivery of the disinfectant solution to the area being treated. Tests have shown that all of the CHG is released from the blended cloths 16 when used for body disinfection.

Various changes can be made to the invention without departing from the spirit thereof or scope of the following claims.

What is claimed is:

1. A method of infection reduction by preparation of a patient before an invasive procedure, comprising:
    a. providing a blended cloth comprising a fibrous mat impregnated with a disinfecting solution having chlorhexidine gluconate (CHG) as an active ingredient and having no alcohol, and
    b. using the impregnated cloth to disinfect at least a portion of the patient up to several days prior to the invasive procedure proximate the location of the invasive procedure, and
    c. releasing all of the CHG from the fibrous mat during step b.

2. The method according to claim 1, in which method step "a" comprises providing a blended cloth comprising first fibers and second fibers, with the quantity by weight of said first fibers generally being greater than the quantity by weight of said second fibers, said blended cloth having an absorbency by weight greater than the weight of said blended cloth.

3. The method according to claim 1, in which step "a" comprises providing a plurality of said blended cloths in a package, and step "b" comprises using each cloth to disinfect a discrete portion of the patient.

4. The method according to claim 1 including the further step of using the disinfecting solution a further time immediately prior to the invasive procedure.

5. The method according to claim 1 in which said fibrous mat consists of polyester fibers.

6. A method of infection reduction by preparation of a patient before an invasive procedure, comprising:
    a. providing a blended cloth comprising a fibrous mat composed of polyester fibers impregnated with a disinfecting solution having chlorhexidine gluconate (CHG) as an active ingredient and having no alcohol, and
    b. using the impregnated cloth to disinfect at least a portion of the patient at least one day prior to, and up to several days prior to, the invasive procedure proximate the location of the invasive procedure.

7. The method according to claim 6, in which method step "a" comprises providing a blended cloth comprising first fibers and second fibers, with the quantity by weight of said first fibers generally being greater than the quantity by weight of said second fibers, said blended cloth having an absorbency by weight greater than the weight of said blended cloth.

8. The method according to claim 6, in which step "a" comprises providing a plurality of said blended cloths in a package, and step "b" comprises using each cloth to disinfect a discrete portion of the patient.

9. The method according to claim 6, in which step "b" includes releasing substantially of the CHG from the fibrous mat.

10. The method according to claim 6 including the further step of using the disinfecting solution a further time immediately prior to the invasive procedure.

* * * * *